United States Patent [19]

Zerhouni

[11] Patent Number: 4,646,334

[45] Date of Patent: Feb. 24, 1987

[54] RADIOGRAPHIC TEST PHANTOM FOR COMPUTED TOMOGRAPHIC LUNG NODULE ANALYSIS

[76] Inventor: Elias A. Zerhouni, 4201 Thoroughgood La., Virginia Beach, Va. 23455

[21] Appl. No.: 818,804

[22] Filed: Jan. 14, 1986

Related U.S. Application Data

[63] Continuation-in-part of Ser. No. 445,462, Nov. 10, 1982.

[51] Int. Cl.$^4$ ............................................. G03B 42/02
[52] U.S. Cl. ...................................... 378/18; 378/207
[58] Field of Search ................. 378/18, 207; 250/505.1

[56] References Cited

FOREIGN PATENT DOCUMENTS 0129037 10/1980 Japan ..................................... 378/18
0129038 10/1980 Japan ..................................... 378/18

Primary Examiner—Janice A. Howell
Assistant Examiner—D. Porta
Attorney, Agent, or Firm—Kerkam, Stowell, Kondracki & Clarke

[57] ABSTRACT

Disclosed is a test phantom for evaluating a computed tomographic scan of nodules in a lung of a human or non-human animal comprising a device which simulates a 15 to 40 mm thick transverse section of said animal the tissue simulating portions of said device are constructed of materials having radiographic densities substantially identical to those of the corresponding tissue in said simulated transverse section of said animal and contain voids therein which simulate, in size and shape, the lung cavities in said transverse section. At least one of the voids has positioned therein a test reference device constructed of a material of predetermined radiographic density which simulates a lung nodule.

9 Claims, 11 Drawing Figures

FAT EQUIV. | FAT EQUIV. | MUSCLE EQUIV. | SPONGIOUS BONE EQUIV | CORTICAL BONE EQUIV

RADIOGRAPHIC TEST PHANTOM FOR COMPUTED TOMOGRAPHIC LUNG NODULE ANALYSIS

RELATED APPLICATION

This is a continuation-in-part of application Ser. No. 445,462 filed Nov. 10, 1982.

BACKGROUND OF THE INVENTION

The discovery of a small rounded mass or nodule in the lung of a patient, usually by chest radiograph, raises the problem of ascertaining whether the mass is malignant or benign. Inasmuch as a benign nodule is usually left undisturbed whereas a malignant nodule requires immediate aggressive therapy, it becomes important to quickly determine the nature of the nodule.

In the past, surgery with resection of the nodule and subsequent pathological analysis were often performed. However, in the early 1950's, it became apparent that a large number of patients were being exposed to unnecessary surgery. Since indiscriminate surgical exploration of lung nodules led to many unnecessary procedures with their attendant mortality and morbidity, less invasive methods of differentiating between a benign nodule of the lung and a malignant tumor were sought. Various research studies indicated that the percentage of benign nodules in a population of patients with newly discovered nodules varied between 40 and 60%.

In the early 1950's, it was also observed that calcified nodules were almost never malignant. Hence radiographic methods to detect the presence of calcifications in lung nodules were developed, in particular linear tomography which blurs the structures above and below the plane of the nodule and permits a better detection of calcification than standard chest radiography. This method has evolved as the main procedure of non-invasive investigation of lung nodules since the late 1950's to the present time.

Others approached the problem differently, by devising methods to obtain small fragments of tissue from the nodule with less risk than surgery. These methods involve bronchoscopy directed biopsy and percutaneous needle biopsy. Although these methods are less risky than surgery, they all entail a significant morbidity albeit at a much lower mortality.

In the early 1970's, a new method of radiographic investigation, termed computed tomography, was introduced. Briefly, this procedure involves positioning a patient between an X-ray source and radiation detectors such that a fan-shaped or pencil-like X-ray beam which is thin in the axial dirction can be projected through the patient. Rotation or displacement of the X-ray source and detectors relative to the patient, results in the development at the detectors of signals indicative of X-ray transmission characteristics or differences in attenuation of the X-ray beam along a plurality of paths through the patient. From these signals it is possible to calculate and print out or record a distribution or matrix of analogs corresponding to the various elements in the body lying in the path of the X-ray beam having differing radiographic densities.

In the case of scanning a lung nodule an image of a transverse section of the patient' chest or torso containing lung tissue is reconstructed based on the above-noted differences in attentuation of the X-ray beam as measured by the detectors at various angles to the object scanned. Computer programs estimate the attenuation of each portion of space of voxel within the X-ray beam by assigning CT numbers to each voxel. These CT numbers are theoretically scaled to the attenuation of water which is the zero value and pure air which is $-1000$. The unit of measurement is termed the Hounsfield (H). The success of this method is fundamentally based on the fact that the CT scanner system is able to differentiate differences in radiographic densities of 0.5 to 1% whereas conventional systems separate densities only if they are different by at least 5 to 10%.

Based on the fact that CT scanners were 5 to 20 times more sensitive to density differencs than conventional radiographic techniques and provided an objective measurement with numbers rather than a subjective visual evaluation of density as with standard techniques, the role of quantitative analysis of the computed tomographic data in patients with lung nodules was investigated. A study involving a large series of patients with mathematical analysis of the density numbers of lung nodules showed that CT scanning was more sensitive in differentiating benign from malignant lung nodules than conventional techniques. It was found that above a certain representative CT number, all lung nodules were benign. It was ascertained that among the nodules which were not considered calcified by standard tomography, a significant percentage (60%) were found to be calcified by computed tomography thereby decreasing the number of unnecessary invasive procedures in these patients who would have otherwise been investigated more aggressively.

Despite the success demonstrated by this study with a particular scanner and a particular method of calculating the CT numbers of each nodule, it quickly became apparent that this method could not be directly translated to other scanners. Several investigators attempted to apply the method using the guidelines and results of the original study but were unable to obtain satisfactory results. A complete analytic study of all factors involved in obtaining correct CT numbers for lung nodules revealed that: (1) CT numbers can vary from scanner to scanner for the same object, (2) CT numbers can vary in the same scanner depending upon the spatial position of the lung nodules investigated, (3) CT numbers can vary from day to day for the same object (temporal drift), (5) the technique used (exposure factors, slice thickness) can change the CT numbers, and (6) the dimensions of the patient's chest can also affect the CT density of a nodule. Further analysis demonstrated that these variations were related to the following:

(1) The computer program used by each manufacturer to reconstruct the images introduces variations in the CT numbers of lung nodules even if the scanners are calibrated with standard available state-of-the-art phantoms which are usually manufactured to give the densities of test objects in water or in plastics but not in air. These differences in computer algorithms also explain the differences in CT numbers obtained for nodules of identical composition but different sizes.

(2) The design of the CT scanner, i.e., third generation versus fourth generation, also influences the CT numbers obtained. It may also explain why CT numbers of the same nodule can vary if the nodule is located in different positions within the scanner.

(3) Depending upon the design of the scanner, the changing characteristics of the X-ray beam as the X-ray tube ages will also introduce errors in measuring CT numbers from day to day.

(4) The CT scanner being a complex electronic machine, variations in the performance of each component as well as the sensitivity of the system to temperature and humidity creates temporal drifts which are very difficult to control. All of these factors explain why it is essentially impossible to correlate the experience obtained on one scanner with that of other scanners since the CT numbers of lung nodules are dependent upon several independent variables. Because of these variations, there exists the need for a simple method of determining the CT density of a lung nodule applicable to all scanners.

Inasmuch as many variables affect the measured CT numbers of a lung nodule, it is necessary to use a standard object of reference against which CT scans of patients with lung nodules can be compared to determine whether the lung nodule is likely to be benign or malignant by virtue of its density. Current phantoms are available in a number of variations, some being plastic replicas of the human body or specific portions thereof while others consist of actual human bones cast in plastics. Recently introduced phantoms include a set of reference samples having known attenuation coefficients surrounded by a water medium housed within a plastic vessel. Phantoms used to calibrate computed tomography systems are usually cylindrical discs having a diameter ranging from 20 to 40 cms. These available phantoms, however, do not simulate the patient's chest with a nodule positioned therein to allow their use as a standard reference phantom for the particular problem of a lung nodule.

Accordingly, it is an object of the present invention to provide a phantom or a reference system against which the density of lung nodules can be compared and their density estimated regardless of the variability factors mentioned above.

SUMMARY OF THE INVENTION

The above and other objects are achieved by the present invention which provides a test phantom for evaluating a computed tomographic scan of nodules in a lung of a human or non-human animal comprising a device which simulates a 15 to 40 mm thick transverse section of said animal, the tissue simulating portions of said device being constructed of materials having radiographic densities substantially identical to those of the corresponding tissues in said simulated transverse section of said animal and having voids therein which simulate, in size and shape, the lung cavities in said transverse section.

The phantom has in association therewith at least one test reference device constructed of a material of predetermined radiographic density which simulates a lung nodule.

The present invention also provides an arrangement or system for evaluating a nodule in the lung of a human or non-human animal by computed tomographic scan of a transverse section thereof containing lung tissue comprising (I) a computed tomography system comprising a radiation source, a radiation detector and means for supporting and positioning said animal between said radiation source and said detector thereby to enable the generation of a computer tomograph; (II) means for supporting and positioning the above-described test phantom between said radiation source and radiation detector thereby to enable the generation of a test computer tomograph whereby to determine the density of a nodule in the lung of said animal by comparison of the respective computer tomographs.

The present invention also provides a method for ascertaining the nature of a lung nodule comprising generating a computer tomograph of a transverse section of a human or non-human animal containing lung tissue, generating a second computer tomograph of the above-described test phantom which simulates the transverse section of the animal and which contains a test reference nodule which simulates in size, shape and position within the lung cavity void the nodule in the transverse section of the animal and comparing the respective tomographs.

DETAILED DESCRIPTION OF THE INVENTION

Figure 1:
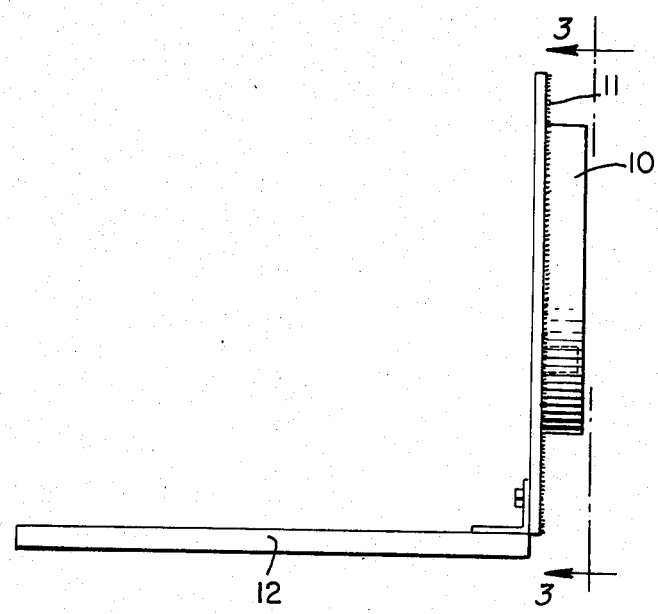
FIG. 1 is a side elevational view of the test phantom device mounted on a support means.

The phantom devices of the invention comprise 15 to 40 mm, preferably about 20 mm thick representative transverse sections of the human torso. One embodiment of the phantom device comprises an approximation of a transverse section of the upper torso or chest. Another embodiment comprises an approximation of the mid torso or chest. A third embodiment comprises a chest approximation of the lower torso. The phantoms are composed of plastics of different formulations which mimic tissue such as spongy bone, cortical bone, muscle, fat, etc., normally encountered in such sections. The transverse sections of organs of the torso are also reproduced in the plastic section. In addition, one or more removable annular devices adapted to be positioned so as to surround the outer circumference of the test phantom device are provided which are constructed of a material having the radiographic density of fat tissue and being of a size and shape so as to simulate outer layers of fat tissue in the transverse section of the animal. Since the charactertistics of the X-ray beam reaching the lung nodule in the chest vary with the size of the patient, the rings are provided to better approximate the attenuation characteristics of the chest wall of an individual patient.

A set of specifically formulated plastic cylinders of different sizes to simulate lung nodules are also provided against which the density of the lung nodule will be compared. The density of this plastic is determined to represent the minimum value above which lung nodules are always benign. These nodules can be placed in any position within the lung field of the phantom to correspond to the position of the nodule in the lung.

In addition, a set of specifically formulated plastic structures of different sizes to simulate various organs of the body are provided for positioning in the phantom device of the invention to coincide with the position of the organ(s) in the patient.

The phantom devices are preferably shaped so as to simulate a transverse section of the human torso when either standing, lying in a supine position or placed in an intermediate position between standing and supine since forces of gravity willk affect the relative position of tissue, orans, bones depending upon the orientation of the torso.

It will also be understood that the particular shapes, thicknesses and distribution of muscle, fat and bone tissue and size of the vertebral body in general vary, depending upon the age of the patient to be diagnosed. Generally, the population of patients examined by computed tomographic scan comprise relatively older, smoking adults. A preferred embodiment of the invention, therefore, comprises a phantom simulating a transverse section of an older adult human.

It will further be understood that the shape and design of the phantom will depend upon the sex of the patient being evaluated since the shapes, thicknesses and distribution of muscle, fat and bone tissue, etc., vary significantly as between males and females.

FIG. 1 is a side elevational view of the test phantom device 10 mounted by means of fiber loops and fiber loop-engaging hooks 11 on support means 12.

Figure 2:
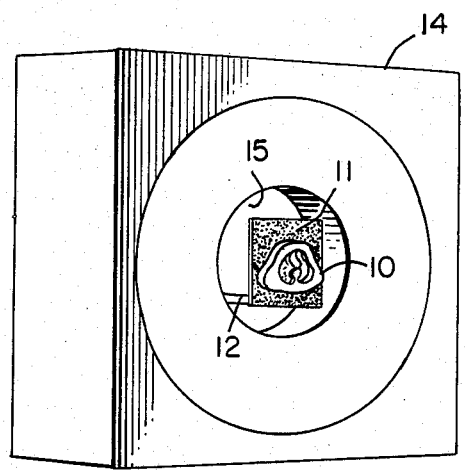
FIG. 2 is a perspective view of the supported phantom with a test reference included positioned in a computed tomographic scanning system.

FIG. 2 is a perspective view of the supported test phantom device depicted in FIG. 1 in position in a computed tomography system generally designated by reference numeral 14 for radiographic scanning. The system is generally vertical having a cylindrical horizontal opening 15 for receiving the patient (not shown) and supported phantom 10.

Figure 3:
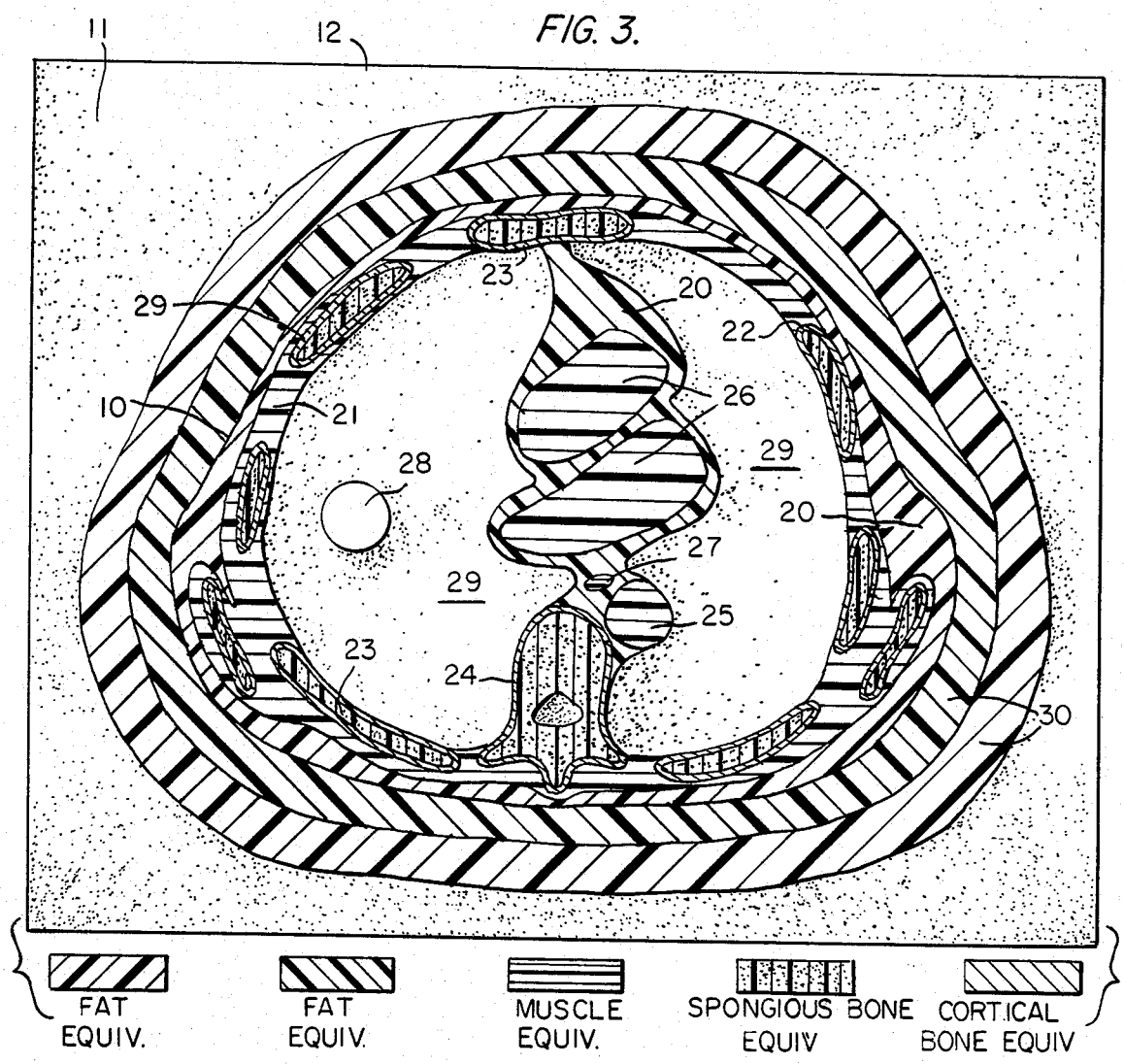
FIG. 3 is an elevational view taken along the line 3—3 of FIG. 1.

FIG. 3 is an elevational view taken along line 3—3 of FIG. 1 showing the test phantom device mounted by means of fiber-loop/fiber loop-engaging hooks 11 to support means 12. In the test phantom device various plastic compositions are employed to simulate in size, shape and radiographic density the fat tissue 20, muscle tissue 21, cortical bone tissue 22, and spongious bone tissue 23 of the transverse section of the lower or mid torso of a human being in a standing position. The particular bone tissue depicted in FIG. 3 is that of the ribs, scapula, sternum and the vertebra 24. The aorta is designated by reference numeral 25 whereas 26 represents sections of the heart. The esophagus is represented by reference numeral 27. The test nodule 28 is positioned by fiber-loop/fiber loop-engaging hooks 11 in the support surface 12 within the lung cavity of the phantom 29.

Additional annular fat tissue simulating rings 30 may be positioned around the outer circumference of the test phantom device via fiber-loop/fiber-loop-engaging hooks 11 to the support surface 12 to simulate outer layers of fatty tissue as needed in the transverse section of the patient undergoing scanning.

FIGS. 4, 5, 6 and 7 are plan views of unsupported test phantom devices 40 simulating various transverse sections of the upper torso of a human being. Again, plastics compositions are formed and molded so as to simulate in size, shape and radiographic density fat tissue 41, muscle tissue 42, cortical bone tissue 43 and spongious bone tissue 44 (here designating the ribs in the simulated transverse section except for vertebra 45, the aortic arch 46, superior vena cava 47, trachea cavity 48, esophagus 49, additional removable fat tissue rings 50, test nodule 51 and lung cavities 52).

Figure 4:
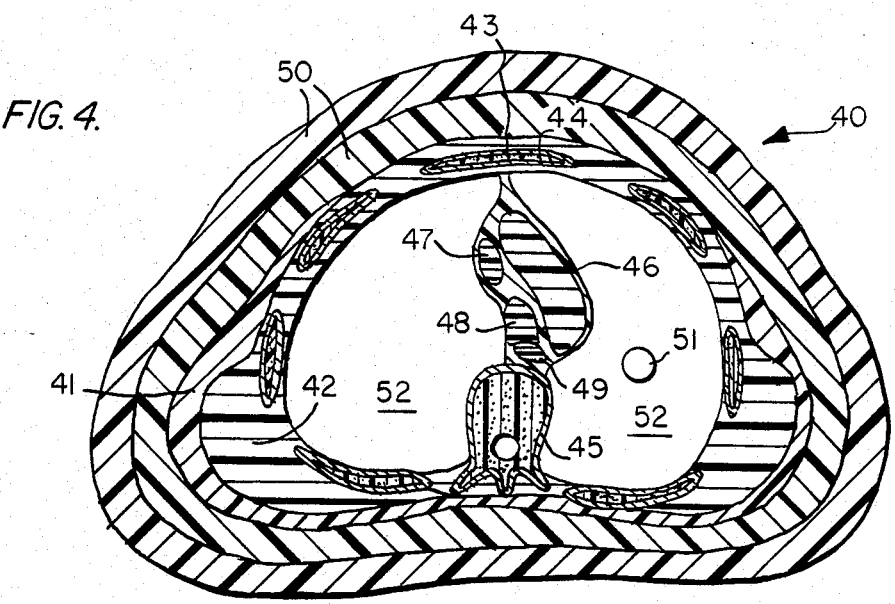
FIG. 4 is a plan view of one embodiment of an unsupported test phantom device.

FIG. 4 is a plan view of a phantom device simulating a transverse section of the upper torso of a standing young adult human being.

Figure 5:
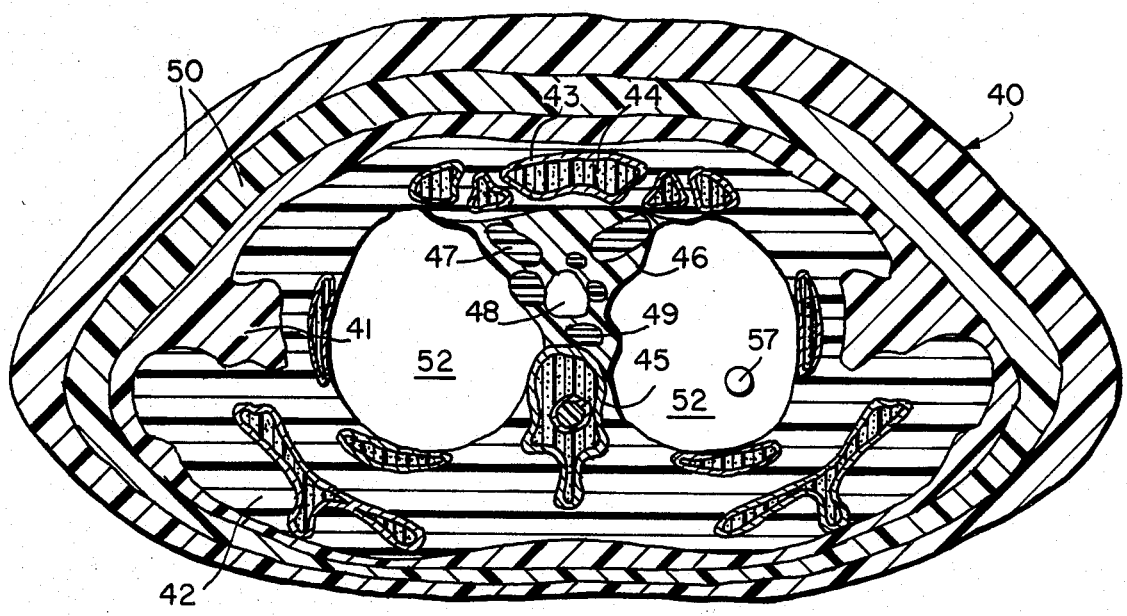
FIG. 5 is a plan view of another embodiment of the test phantom device.

FIG. 5 is a plan view of a test phantom device simulating a transverse section of the upper torso of an older adult human being in a supine position.

Figure 6:
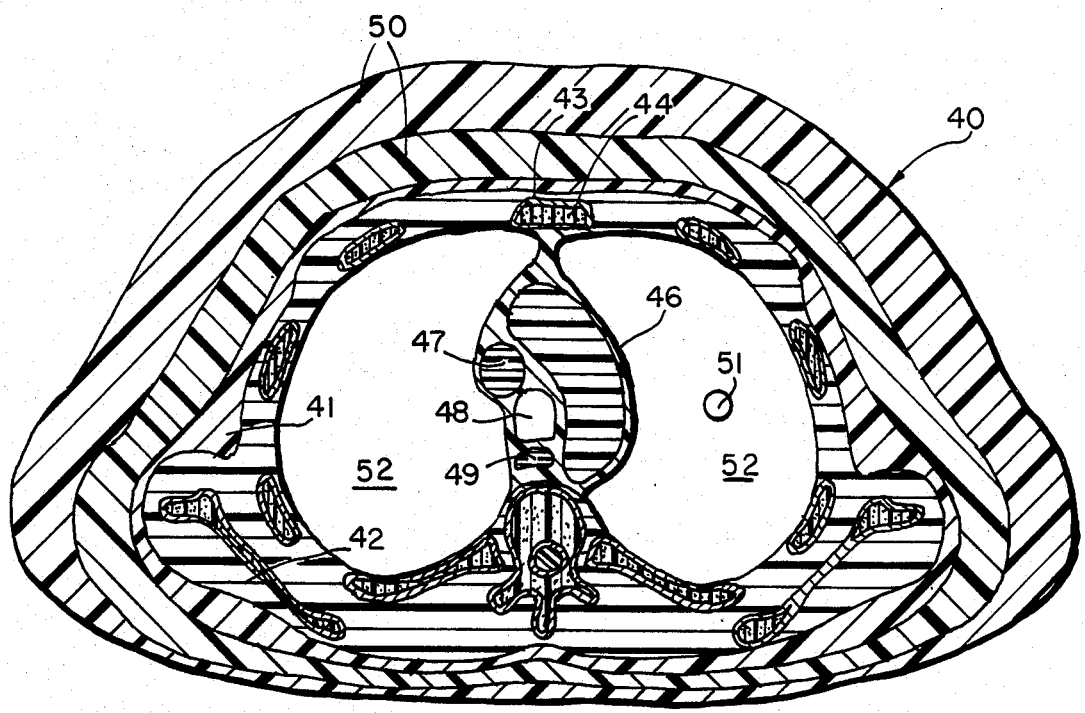
FIG. 6 is a plan view of still another embodiment of the test phantom device.

FIG. 6 is a plan view of a test phantom device simulating a transverse section of the mid torso of an older adult human being in a supine position.

Figure 7:
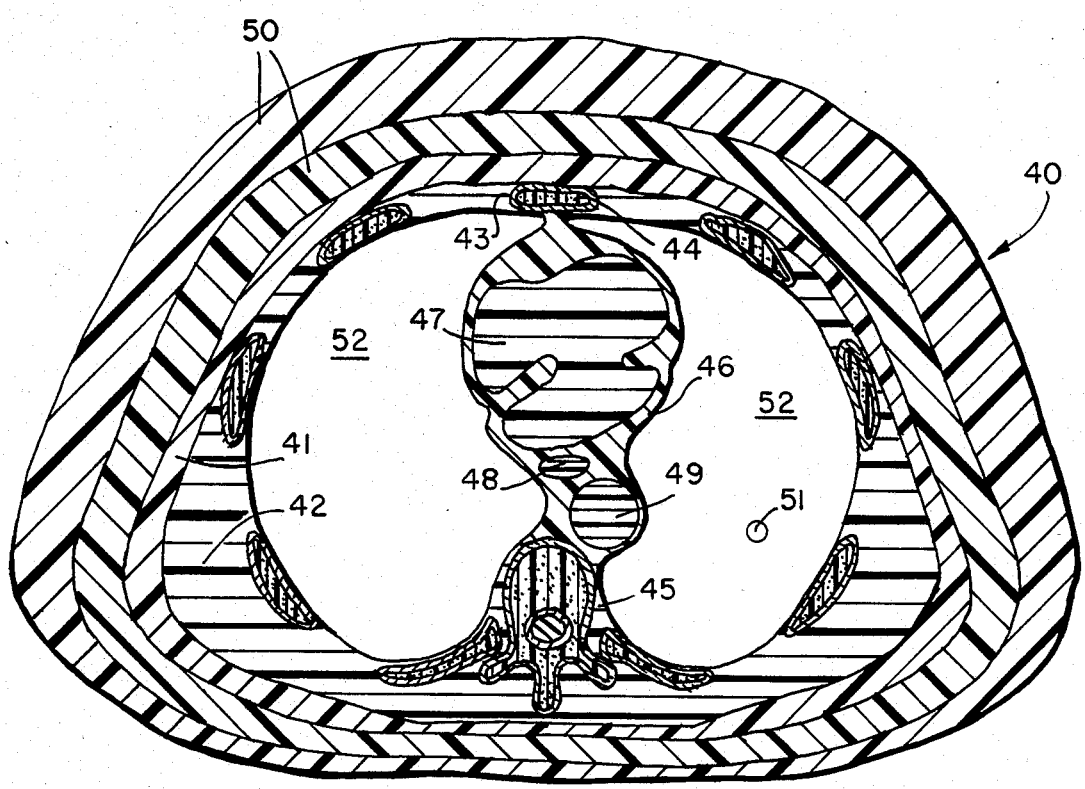
FIG. 7 is a plan view of a further embodiment of the test phantom device.

FIG. 7 is a plan view of a test phantom device simulating a transverse section of the lower torso of an older adult human being in a supine position.

Figure 8:
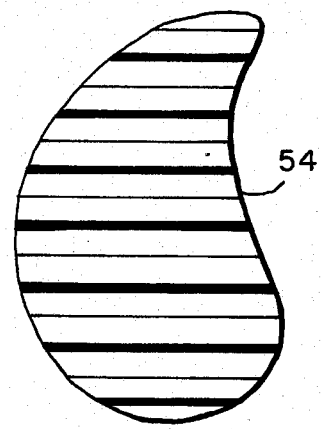
FIGS. 8, 9 and 10 are plan views of transverse sections of test phantom devices of the invention of various shapes and sizes simulating transverse sections of the liver of adult human beings.
Figure 9:
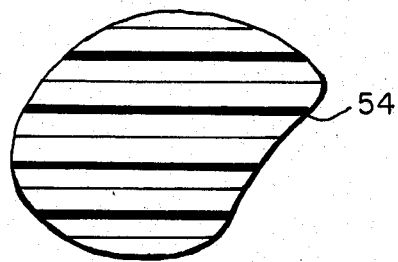
Figure 10:
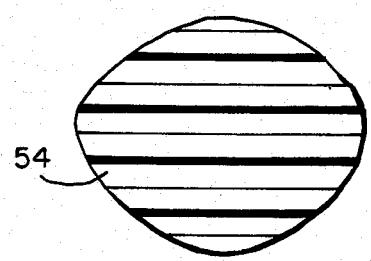

In FIGS. 8, 9 and 10, phantom devices 54 of varying shapes and sizes simulating typical transverse sections of the liver of adult human beings are depicted which may be inserted in any of the test phantom devices of FIGS. 4, 5, 6 or 7 to correspond to the shape, size and position of the liver in the particular transverse section of the patient under examination.

Figure 11:
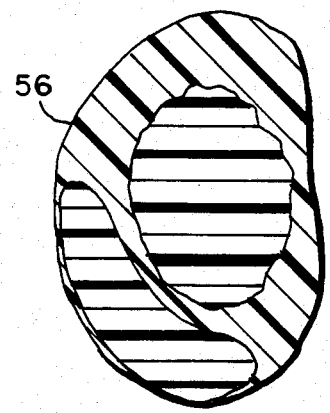
FIG. 11 is a plan view of a transverse section of a test phantom device of the invention simulating a transverse section of the spleen of an adult human being.

In FIG. 11, phantom device 56, simulating a typical transverse section of the spleen and adult human being is depicted which may be inserted in any of the test phantom devices of FIGS. 4, 5, 6 or 7 to correspond to the shape, size and position of the spleen in the particular transverse section of the patient under examination.

The various tissue and organ simulation portions of the test phantom are preferably separately molded in hand-made styrofoam molds utilizing any conventional plastic, mixture of plastics, alone or compounded with appropriate inert fillers to simulate the size, shape and radiographic densities of the various tissues and organs. Suitable plastics include epoxy resins, phenolic rins, polyolefins such as polyethylene, polypropylene, etc.

The plastics are preferably admixed or compounded with fillers such as calcium carbonate or other plastics in microsphere or powder form to increase radiographic density. Molding is usually, and optimally, under vacuum conditions.

Suitable formulations for molding the various tissue and organ sections are as follows: It is to be understood that these formulations are merely representative and that thephantom device may be constructed of any material having a radiographic density equivalent to the particular tissue or organ sections it is employed to duplicate.

A typical "fat-equivalent" material comprises:

| Material | Parts, by weight |
| --- | --- |
| Araldite (diglycidyl ether of bisphenol-A) | 100.0 |
| Jeffamine (polyoxypropylenemine) | 39.9 |
| BJ-930 (phenolic resin microspheres) | 7.9 |
| Carbowax (polyethylene glycol) | 23.9 |

A representative "muscle-equivalent" construction material contains:

| Material | Parts, by weight |
| --- | --- |
| Araldite | 100.0 |
| Jeffamine | 40.2 |
| BJ-930 | 7.9 |

-continued

| Material | Parts, by weight |
| --- | --- |
| Carbowax | 23.9 |
| Calcium carbonate | 23.9 |

A "spongious bone-equivalent" material includes:

| Material | Parts, by weight |
| --- | --- |
| Araldite | 100.0 |
| Jeffamine | 40.8 |
| BJ-930 | 2.0 |
| Carbowax | 20.4 |
| Calcium carbonate | 32.7 |

A typical material for fabricating "cortical bone-equivalent" tissue is as follows:

| Material | Parts, by weight |
| --- | --- |
| Araldite | 100.0 |
| Jeffamine | 40.0 |
| Calcium carbonate | 140.0 |

The "reference standard nodules" may be formed from the following composition:

| Material | Parts, by weight |
| --- | --- |
| Araldite | 100.0 |
| Jeffamine | 40.0 |
| Calcium carbonate | 1.5 |

The phantom is made by successive moldings of the above formulations corresponding to the various anatomical parts corresponding to the transverse section of the animal undergoing evaluation. The manufacturing process requires several steps which are described hereinbelow:

Step 1—A high density styrofoam mold may be hand-carved in the shape and size of the spongious portions of the bones present in the transverse section under consideration. Alternatively, a flexible mold process may be employed for commercial, mass production of the components. The surface of the mold which will be in contact with the plastics is prepared with an appropriate release agent, e.g., silicone grease. The plastic mixture with the composition determined to give the radiographic density of spongy bone is poured in the mold after appropriate preparation, i.e., thorough mixing at the appropriate temperature and under vacuum conditions of the various components of the mixture. The molded parts are allowed to cure for 18 hours at room temperature and for 3 hours at 140 degrees Fahrenheit in an electrical oven. These parts are then de-molded in preparation for the next step.

Step 2—Each spongious bone part is cleaned by thorough washing. Any molding defect is identified and corrected by mechanical means. A thick coat of a mixture of plastics determined to give the density of cortical bone is applied to the parts representing the spongy bone, after appropriate preparation. Two to three coats of cortical bone equivalent plastic are usually needed with a 24 hour cure time between each coat at room temperature followed by three hours of oven curing at 140 degrees Fahrenheit after the last coat.

Step 3—A high density styrofoam mold is hand-carved in the shape of the muscle structures present in the transverse section under consideration. A release agent is applied and the bony parts previously manufactured are then placed in their respective position within the mold and secured in place by tape material. The mixture of plastics that was determined to give the radiographs density of muscle is then poured into the mold. Bonding between the bony part and the newly molded plastic mixture occurs within the curing period of 18 hours at room temperature and 3 hours at 140 degrees Fahrenheit.

After de-molding, the phantom now comprising the muscle parts with the bony parts embedded within them is thoroughly cleaned and molding defects, if any, are corrected.

Step 4—A high density styrofoam mold is hand-carved to imitate the size and shape of the space between the outline of the body and the boundaries of the lung. The release agent is applied and the part molded in step 3 is placed within the mold. The mixture of plastic which was determined to give the radiograph density of fat is then poured in the mold after appropriate preparation as outlined above. This plastic mixture bonds itself to the part manufactured in step 3 after 18 hours of curing at room temperature followed by 3 hours of oven curing at 140 degrees Fahrenheit.

The phantom now comprising all the parts of the transverse section under consideration is de-molded, cleaned and molding defects are corrected.

Step 5—Several high density styrofoam molds are made with an outline conforming to the outline of the phantom obtained after step 4 with a space of 1, 2 or 3 cms. left between the outer margin of the phantom of step 4 and the mold of step 5. The surfaces of the mold as well as those of the phantom of step 4 are prepared with a release agent. Careful attention is directed to preparation of the surfaces of the phantom of step 4 to prevent bonding with the mixture of plastic which will be poured into the mold. The mixture of plastic used is the same as used in step 4. This last step provides a set of removable rings of various dimensions to simulate the attenuation properties of various sized chest walls.

Step 6—A high density styrofoam mold with cylindrical holes of diameter ranging from 0.4 cm to 4 cm in diameter, by 2 mm. increments, is made. The surfaces of the mold are coated with a release agent.

The mixture of plastic which has been predetermined to give the minimum radiograph density at which a lung nodule can be considered benign is poured in the mold after appropriate preparation. Eighteen hours of curing at room temperature followed by 3 hours of oven curing at 140 degrees Fahrenheit are allowed. After de-molding, the plastic rods are cleaned and molding defects are mechanically corrected by appropriate machining.

Step 7—Strips of fibre loop/loop engaging hook material are affixed to various parts of the phantom including the nodules to allow for a fixation of the phantom parts onto the support system of the phantom in any desired position or combination.

The phantom device is utilized as follows:

The patient is first scanned with a technique appropriate to the particular scanner with a slice thickness which is, at most, half the size of the patient's nodule. Several scans of the nodule are obtained. Then, the diameter of the patient's nodule is measured and a reference test nodule of the same diameter is selected. The section of the phantom which best approximates the patient's chest or the level of the lung nodule is then selected (either the high torso section or the low or mid torso section). The thickness of the chest wall of the patient is measured and the appropriate fat ring is added to the phantom section and the whole mounted on the support base. The chosen test nodule and organ simulating devices are then placed in the same position in the appropriate cavities corresponding to the positions of the nodule and organs in the patient. The supported phantom is then placed in the CT scanner in the same configuration and location as the patient. The phantom is then scanned using the identical technical factors (kilovoltage, mA, pulse, and time as well as slice thickness) utilized when scanning the patient. The scan of the phantom is preferably performed immediately after the study of the patient to minimize temporal drift. The scan of the patient in which the lung nodule had the highest density and without motion artifacts is then compared to the scan of the phantom. If the patient's lung nodule is higher in density than the phantom's nodule, the patient's nodule can be considered benign. If the patient's nodule is lower in density than the test nodule, the nodule should be investigated further since the likelihood of the nodule being cancerous in nature is higher.

The determination of whether the phantom's nodule is higher or lower in density than the patient's nodule can be made by two different methods of analysis.

Method I—Numerical Analysis

On most conventional scanners, a printout of the numbers representing a portion of the computer tomographic scan can be obtained. The printouts of the area of the lung nodule of the patient on the scan where the highest CT numbers are observed and with no motion artifacts can be compared with the printout of the area of the test nodule of the phantom. The method of numerical analysis employed is as follows:
1. The total number of voxels representing the nodule of the patient is estimated. As an example, the number is estimated to be 100.
2. Ten percent of this number is then determined; in this example, it equals 10.
3. The average of the 10 contiguous voxels having the highest CT numbers is then calculated.
4. If this average is higher than the CT number of the voxel with the highest value in the printout of the test nodule, the lesion is considered calcified.

Method 2—Visual Analysis

On all conventional CT scanners, computed tomographic scans can be visually analyzed in terms of CT numbers by increments of 1 to 4 Hounsfield (H) units by using a device termed an "electronic window". The width of the window is selected at the narrowest possible width, not to exceed 4H. The scan of the phantom with the test nodule within it is first displayed and the window level moved up to the point at which the test nodule is no longer seen which indicates that all the CT numbers representing the test nodule are below this window level.

The computer tomograph representing the patient's nodule is then displayed utilizing the same window level and window width as found above.

If more than 10% of the total number of voxels representing the patient's nodule are still visualized and if these voxels are contiguous, the lesion can be considered calcified.

Alternatively, on some scanners where it is possible to display two tomographic scans at the same time, the method of analysis may be made much simpler by displaying the scan of the patient with the lung nodule and the scan of the phantom with the test nodule simultaneously. By moving the window level at a very narrow window width, it is simple to determine whether the patient's nodule is lower or higher in density than the test nodule.

It is to be understood that any convenient or conventional means may be employed to position and support the phantom on a suitable support. Preferably, a Velcro system is utilized to support the system. One planar surface of the phantom, fat ring(s) or test nodule(s) is provided with a layer of fiber loops. The phantom engaging surface of the support system (preferably flat) is provided with a layer of fiber loop-engaging hooks. The phantom device, including additional fat ring(s) and test nodule(s) may then conveniently be positioned and moved by merely contacting the engaging surfaces. It will be understood, however, by those skilled in the art, that any surface engaging means can be employed to position and fix the phantom or the support system.

The test phantom of the present invention provides a scanner-independent, technique-independent method for the evaluation of lung nodules against a reproducible standard, as illustrated by the following non-limiting examples:

EXAMPLE 1

A 50-year old white female with a newly discovered 2.5 cm. mass in the upper lobe of the right lung, discovered by a routine chest radiograph, was evaluated as follows:

The patient was placed in a CT scanner with her arms up. The entire chest was examined with 1 cm. thickness sections to exclude the possibility of any other lesions in the remainder of her chest.

A series of 1.5 mm. thick sections at 120 kVp, 4.8 seconds scan time, 600 mA and 2 pulse code were obtained through the lesion at 1.5 mm. intervals. The patient's study was then terminated.

The sections of the patient were examined and that particular section having the highest CT numbers of the nodule were selected. The nodule was in the mid-torsal region of the chest. The mid-torsal section of the phantom was selected for the reference test. The chest wall thickness of the patient was identical to that of the phantom. Thus, no additional fat rings were necessary in this case.

The size of the nodule was measured at 2.5 cms. and a test nodule was selected having a diameter 2.6 cms. The mounting board of the phantom was placed on the CT scanner table. The mid-torsal region of the phantom was affixed to its support in a position identical to that of the patient's when scanned.

The test nodule selected was affixed in the lung fields of the phantom in the same position as that observed on the tomographic scan of the patient. The phantom was then placed in position and a few 1.5 mm. sections of the phantom with the test nodule in place were obtained using the same technical factors as those used with the patient.

The study of the phantom was done immediately after that of the patient. The scan of the patient previously selected and the scan of the phantom with the highest CT numbers were then simultaneously displayed on the scanner. The window width was decreased to 4 and the window level was moved up. At 60 Hounsfield, the patient's nodule had completely disappeared indicating that all of the CT numbers of the nodule were below 60 H. The test nodule was still visible. The conclusion, then, was that the patient's nodule is lower in density than the test nodule,, thereby indicating malignancy, and should be pursued further by more aggressive means. The patient thereafter undewent surgery which showed that the lesion was a cancer of the small cell type.

EXAMPLE 2

A 55-year old patient with a history of bladder cancer was revealed after chest radiographs to have a 1.6 cm. nodule in the right upper lobe.

A complete CT evaluation of the chest was performed with 1 cm. thick sections. No other lesions were seen. A series of 1.5 mm. sections through the nodule were obtained at 120 kVp, 4.8 second scan time, 600 mA and 2 pulse code.

After examination of the patient's scan, the scan with the highest CT number for the nodule was selected.

It was determined that the upper torsal section of the phantom was the most appropriate for this case. Measuring the chest Wall thickness indicated that one additional fat ring measuring 1 cm. in thickness was needed to approximate the patient's chest wall thickness. The 1.6 cm. diameter test nodule was selected.

The phantom was placed on the mounting board in a position identical to that of the patient. The nodule was placed within the right lung field of the phantom in a position identical to that of the patient's nodule. Several scans with a 1.5 mm. thickness and the same technical factors were obtained with the phantom in the scanner gantry immediately after the patient's study.

The two scans were displayed simultaneously. The window width was 4, the window level was moved up. At a window level of 82, the test nodule of the phantom was seen to disappear completely. More than half of the patient's nodule voxels were still visible indicating that more than half of the patient's nodule voxels were higher in density than the test nodule indicating that his lesion was benign. The nodule was later removed surgically and proved to be a granuloma, a benign lesion of the lung which does not require treatment.

I claim:

1. A test phantom for evaluating a computed tomographic scan of nodules in a lung of a human or non-human animal comprising a device which simulates a 15 to 40 mm. thick transverse section of said animal, the tissue simulating portions of said device being constructed of materials having radiographic densities substantially identical to those of the corresponding tissue in said simulated transverse section of said animal and having voids therein which simulate, in size and shape, the lung cavities in said transverse section, at least one of said lung cavity simulating voids having positioned therein at least one test reference device constructed of a material of predetermined radiographic density which simulates a lung nodule.

2. The test phantom of claim 1 wherein said materials of construction comprise plastics.

3. The test phantom of claim 1 wherein the materials of construction of said at least one lung nodule simulating device comprise plastics 4. The test phantom of claim 1 having in association therewith at least one removable annular device adapted to be positioned so as to surround the outer circumference of said test phantom device, said annular device being constructed of a material having the radiographic density of fat tissue and being of a size and shape so as to simulate an outer layer of fat tissue in said transverse section of said animal.

5. The test phantom of claim 1 having means for positioning said phantom device in a computed tomography system to enable a computed tomographic scan of said device through a transverse section thereof.

6. The test phantom of claim 5 wherein said means comprises a first engaging surface in association with a planar surface of said phantom device, said engaging surface being adapted to secure said phantom device to a second engaging surface of a base member in said computed tomography system.

7. The test phantom of claim 6 wherein said first engaging surface is a member of the group comprising:
 I. fiber loops, and
 II. fiber loop-engaging hooks and said second engaging surface is the other member of said group.

8. An arrangement for the computed tomographic scan of a transverse section of a human or non-human animal containing lung tissue and the determination of the density of a lung nodule therein comprising (1) a computed tomography system comprising a radiation source, a radiation detector and means for supporting and positioning said animal between said radiation source and said detector thereby to enable the generation of a computer tomograph; (2) means for supporting and positioning a test phantom between said radiation source and radiation detector thereby to enable the generation of a test computer tomograph said test phantom comprising a device which simulates a 15 to 40 mm. thick transverse section of said animal, the tissue simulating portions of said device being constructed of materials having radiographic densities substantially identical to those of the corresponding tissue in said simulated transverse section of said animal and having voids therein which simulate, in size and shape, the lung cavities in said transverse section, at least one of said lung cavity simulating voids having positioned therein a test reference device of a size and shape corresponding to the nodule in the lung of said animal and positioned in said void of said phantom device at a location corresponding to the location of the nodule in the lung of said animal and the respective computer tomographs compared.

9. In a method for evaluating a computed tomograph scan of a nodule in a lung of a human or non-human animal comprising generating a computer tomograph of a transverse section of said animal containing lung and nodule tissue, generating a second computer tomograph of a test phantom comprising a device which simulates said transverse section of said animal, the tissue simulating portions of said device being constructed of materials having radiographic densities substantially identical to those of the corresponding tissue in said simulated transverse section of said animal and having voids therein which simulate, in size and shape, the lung cavities in said transverse section and which contains a test reference nodule constructed of a material of predetermined radiographic density which simulates in size, shape and position within a lung cavity void of said test phantom the nodule in said transverse section of said animal and comparing the respective tomographs.

* * * * *